United States Patent [19]
Hendry

[11] Patent Number: 5,888,741
[45] Date of Patent: Mar. 30, 1999

[54] COMPUTER-BASED DESIGN AND SCREENING OF MOLECULES USING DNA INTERACTIONS

[76] Inventor: Lawrence B. Hendry, 1939 Bolin Rd., North Augusta, S.C. 29841

[21] Appl. No.: 935,219

[22] Filed: Aug. 22, 1997

Related U.S. Application Data

[60] Division of Ser. No. 369,779, Nov. 28, 1994, Pat. No. 5,705,335, which is a continuation-in-part of Ser. No. 158,689, Nov. 26, 1993, abandoned.

[51] Int. Cl.$^6$ .............................. C12Q 1/68; G06F 19/00; C07C 2/76
[52] U.S. Cl. ........................ 435/6; 364/468.04; 585/360
[58] Field of Search ................................. 435/6; 555/502; 364/468.04; 585/360

[56] References Cited

U.S. PATENT DOCUMENTS

| | | | |
|---|---|---|---|
| 4,461,619 | 7/1984 | Hendry et al. | 434/295 |
| 4,705,796 | 11/1987 | Hendry et al. | 514/328 |
| 5,238,947 | 8/1993 | Hendry et al. | 514/328 |

OTHER PUBLICATIONS

Hendry et al., *J. Steroid Biochem. Molec. Biol.*, vol. 42, pp. 659–670 (1992).
Hendry et al., *J. Steroid Biochem. Molec. Biol.*, vol. 41, pp. 647–651 (1992).
Witham and Hendry, *J. Theor. Biol.*, vol. 155, 42, pp. 55–67 (1992).
Hendry et al., *J. Steroid Biochem. Molec. Biol.*, vol. 39, pp. 133–146 (1991).
Borman, *Chem. Eng. News*, vol. 70, pp. 18–26 (1992).
Brann et al., *J. Steroid Biochem. Molec. Biol.*, vol. 52, pp. 113–133 (1995).
Bransome, *J.Clin. Pharmacol.*, vol. 33, pp. 1147–1148 (1993).
Bransome et al., *J. Theor. Biol.*, vol. 112, pp. 97–108 (1985).
Brooks et al., "Recent Advances in Steroid Hormone Action", *Moudgil, V.K.*, (ed) pp. 443–466, Walther de Gruyter, NY (1987).
Burzynski et al., *Drugs of the Future*, vol. 10, p. 103 (1985).
Copland et al., *J. Steroid Biochem. Molec. Biol.*, vol. 46, pp. 451–562 (1993).
Denton et al., *J. Biol. Chem.*, vol. 267, pp. 7263–7268 (1992).
Hendry et al., *J. Steroid Biochem. Molec. Biol.*, vol. 48, pp. 495–505 (1994).
Hendry, *J. Clin. Pharmacol*, vol. 33, pp. 1173–1187 (1983).
Hendry, *J. Steroid Biochem.*, vol. 31, pp. 493–523 (1988).
Hendry et al., *J. Steroid Biochem.*, vol. 24, pp. 843–852 (1986).
Hendry et al., *Proc. Natl. Acad. Sci. USA.*, vol. 78, pp. 7440–7444 (1981).
Hendry et al., *Perspect. Biol. Med.*, vol. 27, pp. 623–951 (1984).
Hendry et al., "Recent Advances In Chemotherapy", Buchner and Rubinstein (eds), pp. 2498–2499 (1991).
Hendry et al., *J. Steroid Biochem. Molec. Biol.*, vol. 49, No. 4–6, pp. 269–280 (1994).
Hilgard, A.G. and Hummel, D.J. (eds), "Endocrine Bioassay Data", Part III, *U.S. Dept. HEW NIH* (1964).
Lee et al., *J. Med. Chem.*, vol. 35, pp. 258–266 (1992).
Lehner et al., *Molec. Endocrinol.*, vol. 1, pp. 377–387 (1987).
Nardulli et al., *Molec. Endocr.*, vol. 7, pp. 331–340 (1993).
Naruto et al., *Euro. J. Med. Chem.*, vol. 20, pp. 529–532 (1985).
Peters et al., *J. Med. Chem.*, vol. 32, pp. 2306–2310 (1989).
Purdy et al., *J. Med. Chem.*, vol. 33, pp. 1572–1581 (1990).
Rowland et al., *J. Clin. Pharmacol.*, vol. 34, pp. 80–85 (1994).
Steinsapir et al., *American J. Therapeutics*, vol. 1, pp. 236–244 (1994).
Steinsapir et al., *The Endocrine Society*, (74th Annual Meeting), 109, abs 228 (1992).
Tsai and O'Malley, *Ann. Rev. Biochem.*, vol. 63, pp. 451–486 (1994).
Uberoi et al., *Steroids*, vol. 45, pp. 325–340 (1985).
Hendry and Mahesh, *J. Steroid Biochem. Molec. Biol.*, vol. 41, pp. 647–651 (1992).

*Primary Examiner*—Nancy Degen
*Assistant Examiner*—John S. Brusca
*Attorney, Agent, or Firm*—Jones & Askew, LLP

[57] ABSTRACT

It has been discovered that the degree of hormonal activity of candidate ligands correlates better with degree of fit into DNA than with the strength of receptor binding, and that the receptors in the steroid/thyroid hormone/vitamin A and D family alter the physiochemical properties of DNA and in concert with other transcription factors facilitate insertion of the ligand into DNA. As a result, the magnitude of the response is a function of the structure of the ligand as it related to insertion and fit into the DNA and the specificity of the response is a function of the stereochemistry of the receptor through binding to both the ligand and to the DNA. Based on these discoveries, a method is described herein for identifying drugs having increased activity as compared with the natural ligand for receptors such as the estrogenic receptors.

31 Claims, 9 Drawing Sheets

| COMPOUND | 1 | 2 | 3 | 4 | 5 | 6 | 7 | 8 | 9 |
|---|---|---|---|---|---|---|---|---|---|
| Testosterone * | + | | | | | | + | | |
| Progesterone * | | + | | | | | + | | |
| Aldosterone | | + | | | + | | + | | + |
| Cortisol | | + | + | + | + | | + | | |
| Estradiol * | | + | | | | | + | | |
| Triiodothyronine (T₃) * | | + | | | | | +† | | |
| Retinoic Acid * | | | | | | | + | | |
| 1,25-(OH)₂ Vitamin D₃ | + | | | | | | + | | + |

†Salt Bridge

SGI 101

COMPUTER-BASED DESIGN AND SCREENING OF MOLECULES USING DNA INTERACTIONS

This is a divisional of Application Ser. No. 08/369,779, filed Nov. 28, 1994, U.S. Pat. No. 5,705,335, which is a continuation in part of application Ser. No. 08/158,689, filed Nov. 26, 1993, now abandoned.

FIELD OF THE INVENTION

The present invention relates generally to rational drug design, in particular design of biologically active molecules using pharmacophores prepared according to the present invention.

BACKGROUND OF THE INVENTION

Why certain chemical structures and not others are present in nature has been a recurring question raised by scientists since the first organic natural products were characterized. Of equal interest has been elucidating what structural features within any given class of organic molecules are responsible for biological activity. Historically, the lack of satisfactory answers to both questions has relegated the development of biologically active molecules either to serendipity or to exhaustive synthesis and biological testing of large numbers of compounds. This frustration is particularly evident in the pharmaceutical industry where the development of drug agonists and antagonists is often time consuming, tedious and expensive.

This picture is beginning to change as more information is derived from modern molecular modeling techniques including characterization of the active sites in enzymes and the ligand binding sites in receptors. Over the past 15 years, another approach has emerged based upon a series of discoveries made with molecular models, wherein biologically active small molecules have been found to possess complementary stereochemical relationships with gene structure. This approach was first described in U.S. Pat. No. 4,461,619 to Hendry, et al., which is incorporated herein by reference. This simple molecular modeling technology was developed from observations first reported in 1977 of structural relationships between small molecules and nucleic acids, as described by Hendry, et al., *J, Steroid Biochem. Molec. Biol.* 42:659–670 (1992); Copland, et al., *J. Steroid Biochem. Molec. Biol.* 46:451–462 (1993); Hendry and Mahesh, *J. Steroid Biochem. Molec. Biol.* 41:647–651 (1992); Witham and Hendry, *J. Theor. Biol.* 155:55–67 (1992); Hendry and Mahesh, *J. Steroid Biochem. Molec. Biol.* 39:133–146 (1991); Hendry, *J. Steroid Biochem.* 31:493–523 (1988); Lehner, et al., *Molec. Endocrinol.* 1:377–387 (1987); Hendry, et al., *J. Steroid Biochem.* 24:843–852 (1986); Uberoi, et al., *Steroids* 45:325–340 (1985); Bransome, et al., *J. Theor. Biol.* 112:97–108 (1985); Hendry, et al., *Proc. Natl. Acad. Sci. USA* 78:7440–7444 (1981); and Hendry, et al., *Perspect. Biol. Med.* 27:623–651 (1984), all of which are incorporated herein by reference.

The essential ingredient of all genes is a single, well defined polymer, deoxyribonucleic acid (DNA). DNA is a remarkably uncomplicated molecule composed of recurring sugar-phosphate units attached to one of four possible bases: adenine (A), thymine (T), cytosine (C) or guanine (G). The simplicity of gene structure is further evident in the Watson and Crick base pairing scheme of double-stranded DNA (A with T and C with G), and the helical chirality (handedness) dictated by the absolute configuration of the sugar D-deoxyribose. Gene structure could conceivably be composed of many other chemical units, for example, other sugar stereoisomers such as L-deoxyribose or sugar homologs related to D-glucose.

The products of gene structure, proteins, are also simple, ubiquitous molecules. Nature limits the structure of proteins by constructing them from only twenty basic units, the amino acids; protein chirality is constrained by the absolute L-configuration of the amino acids. As in the case of nucleic acid subunits, a wide range of structural alternatives are possible for protein amino acids. Examples include changes in the chirality of a given amino acid side chain (e.g., D-isoleucine), rearrangements in the pattern of atoms (e.g., the t-butyl isomer of isoleucine) or the addition of atoms (e.g., pipecolic acid, a homologue of proline).

Structural constraints are also evident in the stereochemistry of low molecular weight natural products. Particularly conspicuous are limitations imposed by nature on the number, size, shape, elemental composition, and chirality of biologically active small molecules. For example, the pervasive neurotransmitters histamine and serotonin are unique in that alternative structures with changes in the position or composition of heteroatoms and/or ring patterns generally do not exist in nature. Similarly, many small molecular weight hormones are few in number, have recurring structural patterns and possess a single absolute chirality.

The source of the pervasive occurrence of physicochemical constraints on the structure of naturally occurring small molecules lies directly in the structure of the proteins which govern both their biosynthesis and bioactivity, i.e., enzymes and receptors, respectively. Ultimately, however, this stereochemical information is contained in the genes. According to the basic tenants of molecular biology, the information in DNA is replicated with remarkable precision and fidelity into newly synthesized DNA. It is also transcribed into RNA and subsequently translated into protein.

This scenario, however, presents an apparent paradox. While the genetic template ultimately directs which proteins and small molecules are synthesized, as well as which proteins and small molecules will interact with each other, the undirectional flow of genetic information during translation suggests that DNA structure performs this function without recognizing the structure of the small molecule. With few exceptions, such as certain antibiotics which bind directly to DNA and block transcription, small molecules are not considered to recognize or interact with the genetic template. Moreover, the structures of the molecules that are biosynthesized are thought to be unrelated to the structure of the genes.

In the initial search for structural relationships between biologically active natural products and DNA, it became apparent that the two-dimensional structures of DNA base pairs were analogous to many classes of small molecules, including gibberellic acid, a phytohormone; benzo [a] pyrene oxide, a carcinogen; the prostaglandin $PGE_2$; morphine, a narcotic; estradiol, a hormone; riboflavin, vitamin $B_{12}$; serotonin, a neurotransmitter; and actinomycin, an antibiotic. In addition to similarities in size and shape, numerous small molecules contained donor/acceptor functional groups at locations where hydrogen bonds occurred between the base pairs. When overlaid on the base pairs, some compounds, such as the plant hormone gibberellic acid, the steroid hormone estradiol, and prostaglandins, contained heteroatoms separated by internuclear distances similar to that of phosphate oxygens on adjacent strands of double-stranded DNA. This was particularly evident in functional groups attached at the 3 and 17β positions of the steroids.

Using three dimensional Corey-Pauling-Koltun (CPK) space filling models, it became apparent that there were spaces between base pairs in partially unwound DNA that could accommodate a variety of small molecules. For example, estradiol could be inserted between base pairs in DNA, and the hydroxyl groups at 3 and 17β of estradiol were positioned such that they could form hydrogen bonds to phosphate oxygens on adjacent strands of DNA. Other steroids, including testosterone and progesterone, were also capable of stereochemical insertion between base pairs. In each case, complementary donor/acceptor linkages could be formed and the steroid conformed well to the topography of the double helix. Attempts to insert any of the non-naturally occurring steroid enantiomers into DNA resulted in poor fit in that donor/acceptor linkages were strained or could not form, and/or the overall shape of the molecules was incompatible with the helical topography of the DNA.

Certain synthetic compounds with hormonal activity can also be accommodated within the DNA; in many cases, the fit of synthetic compounds such as diethylstilbestrol mimicked that of the natural hormone. In addition to mammalian steroids, prostaglandins, the insect hormone ecdysone and several phytohormones were also capable of stereochemical insertion and "recognition" by the double helix. In the case of the plant hormone gibberellic acid, four stereospecific hydrogen bonds could be formed to donor/acceptor positions on the DNA. As with the steroids, only the naturally occurring enantiomer of gibberellic acid conformed to the topography of the double helix.

One conclusion drawn from these studies is that certain chemical shapes, coupled with heteroatom positioning compatible with that of the phosphate backbone of DNA and hydrogen bond positions of the base-pair template, potentiate partial or complete recognition between biologically active molecules and DNA.

While it was possible to form complexes between DNA and a variety of molecules, amino acids did not initially show any clear accommodation to the space between base pairs. Certain compounds derived from amino acids, for example, neurotransmitters, fit into related sites.

These relationships have been described as a stereochemical logic associated with gene structure. The stereochemical logic is defined as those unique features of nucleic acid structure which ultimately dictate constraints on molecular structure, function, metabolism, and biologic activity.

The use of molecular modeling as a tool to study organic structure has dramatically increased due to the advent of computer graphics. Not only is it possible to view molecules on computer screens in three dimensions but it is also feasible to examine the interactions of ligands with various macromolecules such as enzymes and receptors, as reviewed by Borman, *Chem. Eng. News* 70:18–26 (1992). An almost baffling array of software and hardware is now available and virtually all major pharmaceutical companies have computer modeling groups which are devoted to drug design.

Modern methods of drug design include studies which focus on the binding of a molecule to a protein such as a polypeptide ligand for a receptor, or a steroid such as an estrogen or progesterone for a receptor. Similarly, drugs can be designed based upon the interaction of substrates with various enzymes. For the most part, however, binding sites in proteins have been difficult to characterize. There are many situations where other mechanisms must be involved to explain the feedback between protein regulation and regulation of gene expression.

What is needed is a method for accurately predicting the biological activity of a given compound. The method should be easy to perform and should be able to predict both agonist and antagonist activity.

SUMMARY OF THE INVENTION

The present invention is a method for idenitifying biological activity of molecules using pharmacophores. According to the present invention, molecules are screened by determining the degree of "fit" in the pharmacophore.

The method according to the present invention can be used to identify drugs having increased biological activity or which have usefulness as antagonists or agonists, including, for example, estrogens and anti-estrogens. This method can also be used for the following: to predict the fit of compounds into nucleic acids, especially DNA; to predict the bioactivity of compounds, to screen compounds for toxicity; to design chemical groups to add to specific sites on molecules to facilitate metabolism or render the drug an agonist or antagonist; and to create molecules that mimic the activity of the DNA binding regions of receptors.

The present invention also includes pharmacophores and the method of producing the pharmacophores and the use of the pharmacophores in predicting biological activity of a given compound. The present invention also includes the design of biologically active molecules using the pharmacophore.

It is therefore an object of the present invention to provide a method which can be used to design a biologically active molecule.

It is another object of the present invention to provide a method to screen and/or evaluate existing compounds for toxicological activity.

Still another object of the present invention is to provide a method to predict the toxicity of compounds.

Another object of the present invention is to provide a method to predict the toxicity of compounds for specific organs, tissues, and cells.

Yet another object of the present invention is to provide a method to design compounds that will have particular types of biological activities, including, but not limited to, hormonal, neurotransmitter, metabolic, genetic, immunologic, pathologic, toxic, and anti-mitotic activities.

Still another object of the present invention is to provide a method to predict the bioactivity of compounds including, but not limited to estrogenic, anti-estrogenic, androgenic, anti-androgenic, progestational, anti-progestational, mineralocorticoid, retinoid, vitamin D like, thyroid, and glucocorticoid bioactivities.

Yet another object of the present invention is to provide a method to create pharmacophores that can be used to design compounds such as drugs, hormones, neurotransmitters, agonists and antagonists more efficiently and economically.

It is another object of the present invention to provide a method to create receptor pharmacophores that are molecular models of the portions of receptor molecules that bind to nucleic acids.

Yet another object of the present invention is to provide a receptor pharmacophore that can be used to design molecules that bind to nucleic acids with different affinity than the receptor.

Yet another object of the present invention is to provide a pharmacophore that represents the three dimensional arrangement of solvent molecules around the ligand pharmacophore that binds to nucleic acids.

Another object of the present invention is to provide a pharmacophore that represents the three dimensional arrangement of solvent molecules around the receptor pharmacophore that binds to nucleic acids.

It is yet another object of the present invention to provide a method to create a pharmacophore that is a three dimensional model of the nucleic acid binding domain of the receptor and of the ligand molecule that binds to the receptor and interacts with the nucleic acid at a different site.

Another object of the present invention is to provide a pharmacophore that represents the three dimensional arrangement of molecules that can be attached to other pharmacophores to modify their biological activity.

Still another object of the present invention is to provide a pharmacophore that represents the three dimensional arrangement of molecules that can be attached to other pharmacophores in order to design sites for enzymatic cleavage.

These and other objects, features and advantages of the present invention will become apparent after a review of the following detailed description of the disclosed embodiments and the appended claims.

BRIEF DESCRIPTION OF THE FIGURES

The file of this patent contains at least one drawing executed in color. Copies of this patent with color drawings will be provided by the Patent and Trademark Office upon request and payment of necessary fee

DETAILED DESCRIPTION OF THE INVENTION

Figure 1:
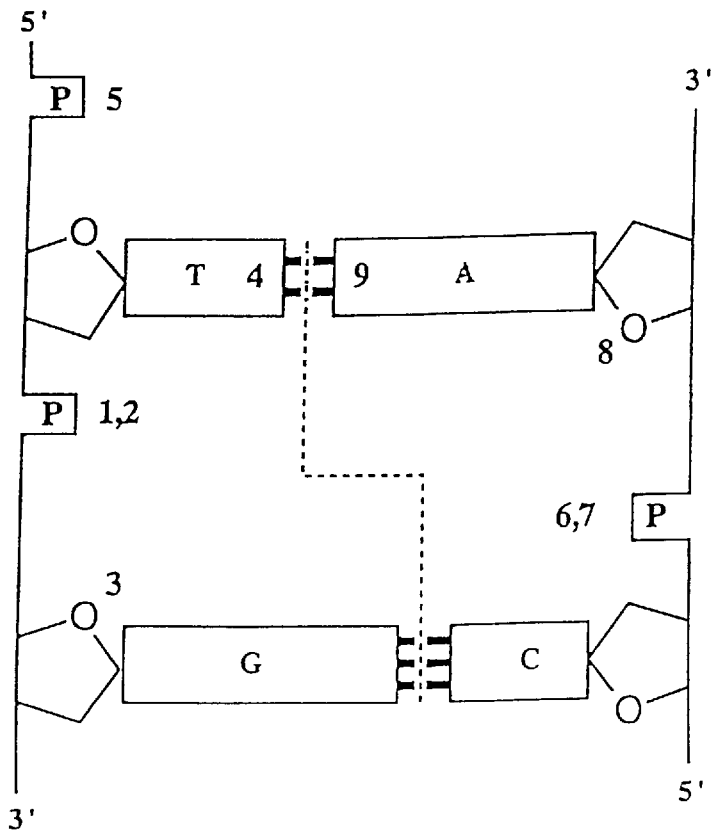
FIG. 1 is a schematic of a cavity in DNA and the numbered sites which accommodate steroid/thyroid/vitamin A and D ligands: testosterone (1,7); progesterone (2,7); aldosterone (2,5,7 and 9); cortisol (2,3,4,5, and 7); estradiol (1 and 6); triiodothyronine ($T_3$) (1 and 6); retinoic acid (6); and 1,25- $(OH)_2$ vitamin $D_3$ (1 and 6); these are divided into two groups based on their interaction with either site 6 or 7.
Figure 2:
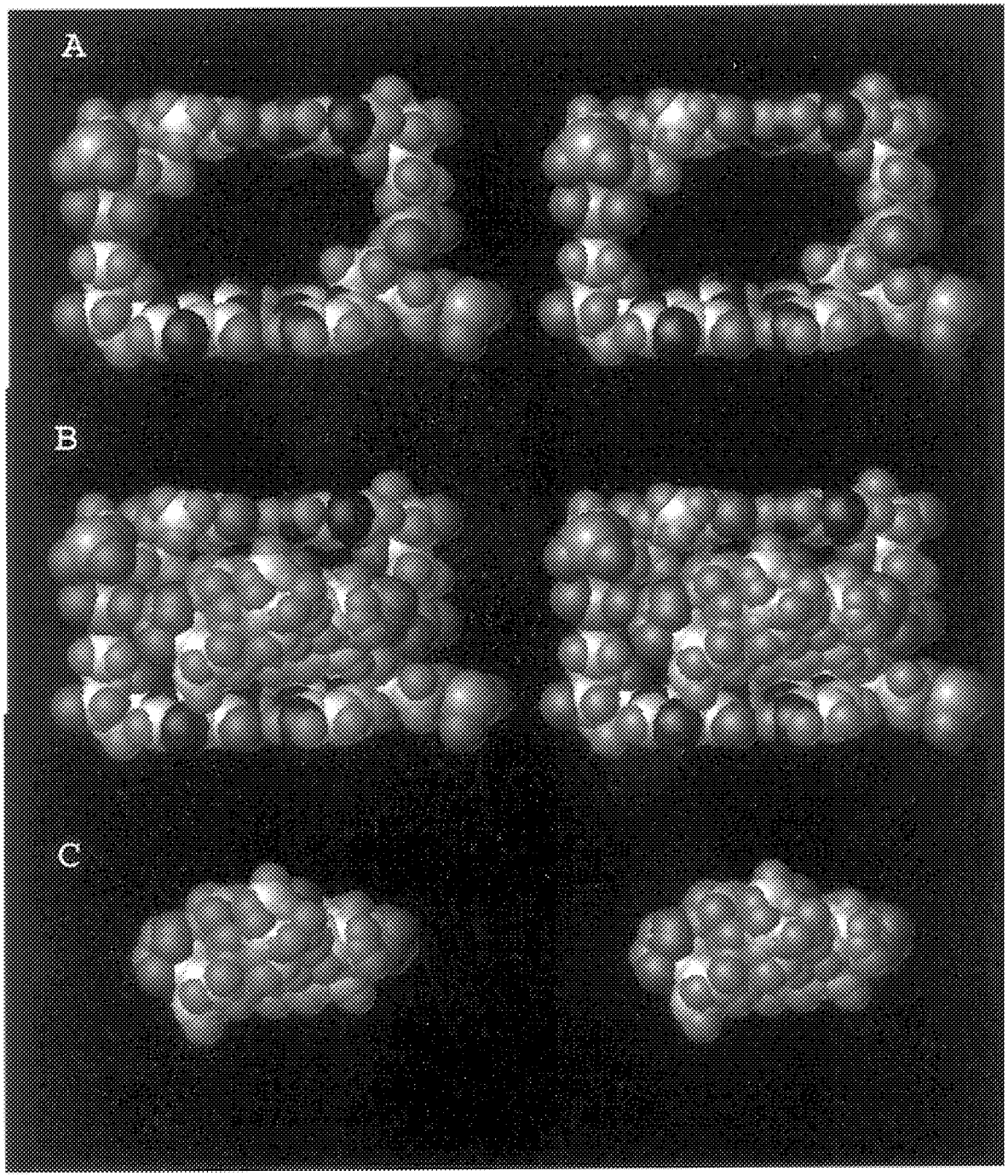
FIGS. 2A–2C depict a computer generated space filling stereo view of the DNA cavity (A), which fits active estrogens oriented by energy calculations into the DNA cavity (B), whereas (C) shows the combined active surface of estrogens removed from the cavity in DNA that is used to construct the pharmacophore.

Many natural products have structures that exhibit stereochemical complementarity with nucleic acids, including amino acids, phytohormones, cyclic nucleotides, prostaglandins, insect hormones, steroid hormones, neurotransmitters, sugars, peptide hormones, thyroid hormones, pheromones, and vitamins. A striking example is the cyclopentanophenanthrene motif repeated in all classes of mammalian steroid hormones, such as estrogen and progesterone. Another example is the kaurene nucleus containing eight chiral centers which is evident in the gibberellin class of plant hormones.

There are many ways to examine the stereochemistry of various configurations and conformations of nucleic acids. For example, Silastic polymer models can be constructed based upon computer derived space filling x-ray coordinates to reflect the stereochemistry of partially unwound DNA/RNA complexes, RNA—RNA complexes, ent-DNA (mirror image of DNA made with L-deoxyribose), and apurinic/apyrimidinic sites in DNA. These cavities reveal a sequence specificity in the fit of many molecules. The apurinic/apyrimidinic sites accommodate amino acids according to the known genetic code. The plant hormone gibberellic acid fits best into the partially unwound site 5'-dTdA-3', 5'-dTdA-3'; members of the mammalian steroid/thyroid hormone superfamily fit best into 5'dTdG-3', 5'-dCdA-3'. Each class of mammalian hormone forms unique stereospecific donor-acceptor hydrogen bonds with DNA. The capacity to fit within these cavities in the manner of the index biologically active molecule correlates with the degree of biologic activity. It is not possible to fit chiral naturally occurring molecules into ent-DNA. However, ent-DNA accommodates the biologic unknown chiral enantiomers, such as ent-progesterone.

According to the present invention, computer modeling is used to examine the relationships between compounds and their fit in helical DNA. Although described herein with reference to double stranded, helical DNA, many of the same principles are applicable to double stranded RNA, and/or to RNA-DNA hybrids. Unless otherwise specified, double stranded RNA and DNA are to be considered equivalents as used herein. Computer modeling can be used to view the interactions of molecules as well as to measure the energy of a given interaction. While a variety of software packages are available for computer modeling of molecules, a preferred software package is Sybyl software (version 6.03; Tripos Associates, St. Louis, Mo.) for measuring the docking of various small molecular weight ligands into DNA. In the examples described herein, the software is run on a Silicon Graphics Indigo Extreme equipped with hardware stereo, i.e., Crystal Eyes (StereoGraphics, San Rafael, Calif.). Structures of small molecules are obtained via: the Cambridge Crystallographic Database, Lanfield Rd., Cambridge, England; construction with the Concord program or from fragment libraries and/or modifications of existing x-ray structures followed by energy minimization. All energy calculations are made using the Sybyl force field with a 1.2 Å van der Waals parameter for hydrogen, as described by Hendry, et al., *J. Steroid Biochem. Molec. Biol.* 42:659–670 (1992) and Hendry, et al., *J. Steroid Biochem. Molec. Biol.* 39:133–146 (1991). Charges are calculated using the Gasteiger-Huckel method to include σ and π bonding. Partially unwound DNA cavities of various double stranded dinucleotide sequences are constructed from the Watson and Crick canonical B form of DNA by twisting each of the fourteen torsional angles along the sugar-phosphate backbone while maintaining the structural integrity of hydrogen bonds between the base pairs. The 3'-endo deoxyribose conformation of the sugars is employed and Kollman charges are calculated. Within these constraints, attempts are made to adjust the degree of unwinding and the resulting degree of separation of the base pairs to accommodate the width of various ligands Each ligand is inserted into the cavity in DNA using van der Waals dot, mesh, and space filling surfaces in stereo to guide the docking procedure and minimize steric strain. The oxygens of the phosphate groups are permitted to act either as proton donors or acceptors and oriented to maximize the fit of any given ligand. The docking of the molecules is repeated several times. The distances between heteroatoms are monitored interactively to optimize the direction and distances of potential hydrogen bonds. While evaluating fit of compounds in a given hormone class, attempts are made to insert all candidate ligands into the DNA sequence with donor/acceptor linkages common to the hormone. Donor/acceptor relationships are further maximized by appropriate orientation of functional groups on the ligands, e.g., by adjusting the conformation of each structure to best mimic the fit of the hormone.

Van der Waals interactions of the candidate ligands are optimized with the DNA surface. The force field is used to calculate the relative fit of each ligand by assessing the optimum favorable energy change resulting from docking the ligand. Each ligand is docked into the DNA and the steric fit is calculated from the change in van der Waals energy; the hydrogen bonding fit is calculated from the change in electrostatic energy using charges on donor hydrogens and acceptor heteroatoms. The energy changes are assessed for each ligand. The greater the negative energy change upon insertion of a given ligand into DNA, the more favorable the fit and the more stable the complex. Optimal docking is determined when no further increase in fit is observed. The most favorable change in energy is selected to compare the relative fit of each molecule. The overall fit of each ligand is assessed by adding the change in kcal of the van der Waals and electrostatic energies and normalizing the fit to that of the parent hormone.

Complementarity of Biologically Active Structures

Although not wanting to bound by the following hypothesis, it is believed that the mechanism of action of hormones in the steroid/thyroid superfamily where ligand bound receptor is known to regulate hormone responsive genes is mediated by physically inserting small molecules into DNA. The prior art teaches that the ligand causes a specific conformational change in the receptor protein which in turn contacts the DNA resulting in gene regulation. In contrasts according to the present invention, there is a receptor-mediated insertion of the ligand into DNA. This is consistent with the widely reported lack of correlation between hormonal activity and receptor binding for estrogenic steroids. According to Brooks, et al., *Recent Advances in Steroid Hormone Action*, Moudgil, V. K. (ed) 443–466 (Walther de Gruyter, NY 1987), who made an extensive study of estrogen structure-function relationships, receptor binding is essential for target-cell responses elicited by the steroids. However, the affinity of altered estrogens is not directly related to the character or extent of the response. At the same time, the binding of estrogens and other steroids to DNA in the absence of receptor has been observed to be weak by numerous investigators. These include studies of the flat phytoestrogen coumestrol which might be expected to easily slide between base pairs. In short, the binding of the steroid independently to either the receptor or the DNA does not appear to be sufficient to fully explain hormonal response.

Several pieces of evidence indicate that certain molecules, such as steroids, that have been shown to fit remarkably well between base pairs in DNA may elicit strong biological responses albeit through relatively weak interactions with DNA. Support for this concept is based on in vitro and in vivo experimental data and the energy calculations demonstrating a correlation between fit of estrogens into DNA and uterotropic activity, for example, studies of a new class of antitumor agents which have led to the discovery of drugs that are potent but act by binding weakly to DNA via intercalation, reported by Lee, et al., *J Med. Chem.* 35:258–266 (1992). Additional support that binding to receptors alone is insufficient to explain activity is provided by the observation of poor binding of a potent estrogen analog, 11β-acetoxyestradiol, which is considerably more active than estradiol.

In general, given that degree of hormonal activity does not always correlate well with receptor binding but does correlate with fit into DNA, it follows that the mode of action of steroids involves a stage(s) in which the ligand is recognized by both the receptor and the DNA. This conclusion has also been reached in studies of anti-androgens.

It is contemplated as part of the present invention that binding of the steroid to its receptor serves as a means to recognize the general class of hormone (e.g., estrogen versus androgen) whereas the type and degree of the fit of the steroid in the DNA is largely responsible for governing the magnitude of the biologic response. The steroid alone is incapable of proper insertion into DNA either in vivo or in vitro without the receptor and thus would be unable to generate a full hormonal response without the receptor A potentially critical role for the receptor upon binding to DNA possibly in concert with other transcription factors, is to regulate the physicochemical properties of the site in DNA to permit insertion of the steroid, including the degree of unwinding, the capacity of heteroatoms to act as either donors or acceptors, and the pattern and degree of solvation. This is further supported by the decrease in the surface hydrophobicity of the receptor upon binding estrogens and antiestrogens as well as phosphorylation which enhances binding of the estrogen receptor to specific DNA sequences, reported by Denton, et al., *J. Biol. Chem.* 267:7263–7268 (1992).

The process of a receptor-mediated insertion of steroids into DNA presumably involves several steps. For example, in the case of estrogens, the initial contact of the DNA by the steroid-receptor complex could involve a partially exposed D ring of the steroid with the A ring still attached to the receptor. Analysis of receptor binding data supports this possibility. Stereospecific recognition of the DNA by partial insertion and hydrogen bonding of the 17β-hydroxyl of the steroid D ring with the 5'-dTdG-3' strand could be followed by complete insertion and the recognition within the double helix manifest by the linkage of both stereospecific hydrogen bonds. The weak binding observed for the steroids with DNA suggests that the steroid/DNA complex might be short lived and rapidly reversible. Certain estrogen antagonists which are accommodated differently in DNA may form longer lived interactions within the site.

There are numerous possible scenarios and implications of receptor mediated binding of ligands to nucleic acids. For example, the lack of effectiveness of certain anti-estrogens in tissues which lack estrogen receptor might be due in part by the inability of the antagonist to be transported to the DNA obviating the insertion of the ligand. Mutation of the site which accommodates the estrogens would also result in improper recognition of the ligand and would be predicted to no longer permit the gene to be properly regulated either by agonists or antagonists. There might be multiple levels at which a given compound might act, as suggested by the observation that cavities in double stranded RNA and RNA-DNA hybrids can accommodate various ligands, for example, estradiol in 5'-rUrG-3', 5'-dCdA-3'.

Molecular Modeling

Molecular modeling was performed with Sybyl/Mendyl 5.4 (Tripos Associates, St. Louis, Mo.) using an Evans and Sutherland PS390 graphics computer equipped with a stereographic viewer. Structures of piperidinedione ligands were provided via construction with the Concord program or from fragment libraries followed by energy minimization. Energy calculations were made with Sybyl/Mendyl force field and a 1.2A van der Waals parameter for hydrogen. Charges were calculated using the Gasteigner-Huckel method which includes σ and π bonding. Partially unwound DNA was constructed with 3'-endo deoxyribose conformation and Kollman charges. This method has been described by Hendry, et al., *J. Steroid Biochem. Molec. Biol.* 42:659–670 (1992); Hendry, et al., *J. Steroid Biochem. Molec. Biol.* 39:133–146 (1991), and Hendry et al., *J. Steroid. Biochem. Molec. Biol.* 49: No. 4–6, pp. 269–280 (1994) the teachings of which are hereby incorporated by reference in their entirety.

The ligands were inserted into the cavity in DNA using van der Waals dot surfaces and the stereoviewer to guide the docking procedure and minimize any obvious steric strain. The distances between heteroatoms were monitored interactively to optimize the direction and distances of potential hydrogen bonds. Donor/acceptor relationships were further maximized by appropriate orientation of functional groups on the ligands, e.g., by adjusting the conformation of each structure. Attempts were made to optimize van der Waals interactions of the candidate ligands with the DNA surfaces. The force field was used to assess the relative fit of each ligand by quantitating the optimum favorable energy change resulting from docking the ligand. Steric fit was calculated from the change in van der Waals energy, the hydrogen bonding fit was calculated from the change in electrostatic energy using charges on donor hydrogens and acceptor oxygens. The greater the negative energy change upon insertion of a given ligand into DNA, the more favorable the fit and the more stable the complex. Docking was completed when no further increase in fit was observed. The most favorable change in energy was selected to compare the relative fit of each molecule. The overall fit of each ligand was assessed by adding the change in kcal of the van der Waals and electrostatic energies and normalizing the value to that of the best fitting molecule (100%). It should be noted that while the energies reported here were derived from widely used force field calculations, they were not empirically derived. Thus, the absolute values in kcal do not have independent experimental significance. At the same time, they are valuable indicators of the relative degree of fit into DNA of candidate molecules.

Previous studies using space filling models indicated that 3-phenylacetylamino-2,6 piperidinedione was capable of fully inserting between base pairs in DNA and forming a stereospecific hydrogen bond between the imino proton of the piperidinedione ring and a negatively charged phosphate oxygen on the deoxyribose-phosphate backbone. Results employing computer graphics confirmed this observation. Energy calculations further demonstrated that this compound had favorable van der Waals contacts of approximately −17.7 kcal when inserted into DNA with an electrostatic energy of approximately −21.7 kcal resulting from the stereospecific hydrogen bond (2.7 Å) to phosphate. Increased fit of the ligand was obtained by substituting a para hydroxl group on the phenyl ring; this substitution enabled a second hydrogen bond to be formed between the hydroxyl group and a phosphate oxygen on the adjacent DNA strand. The increase in fit measured by energy calculations due to the second hydrogen bond (2.64 Å) was reflected in an additional −24.6 kcal in electrostatic energy. Other substitutions which were made on the 3-phenylacetylamino-2, 6-piperidinedione skeleton did not significantly increase fit demonstrated by the normalized energy calculations for certain halogenated analogs.

Synthesis

The synthesis of the unsubstituted derivative, 3-N-phenylacetylamino-2,6-piperidinedione has been briefly described by Burzynski, et al., *Drugs of the Future* 10:103 (1985), and was used as a general method for the preparation of the desired compounds. Appropriate phenylacetic acids were reacted with N-hydroxysuccinimide in the presence of N,N-dicyclohexylcarbodiimide (DCC) which gave succinimide esters. The active esters were stable enough to isolate for physical and spectroscopic characterization although the major portions of the esters were used for the next reaction without purification. The active esters were reacted with L-glutamine in the presence of sodium bicarbonate to obtain the glutamine derivatives. However, due to the difficulties of obtaining the analytical samples, crude products were directly used for the next reaction. To prepare active esters, the glutamine derivatives were again reacted with N-hydroxysuccinimide in the presence of DCC to give the active esters which without purification were heated at 95°–100° C. to obtain the desired 2,6-piperidinediones in various yields. During the heating process the compounds were racemized.

Biological Evaluation

These synthetic derivatives were assessed for biological potency by measuring their growth inhibitory effects on various cell lines using concentrations of 4 nM based on the reported $IC_{50}$ of 3-phenylacetylamino-2,6 piperidinedione in Nb2 cells. In YAK lymphoma cells, the p-hydroxy compound was the most active derivative. This compound, p-hydroxy-3-phenylacetylamino-2,6-piperidinedione was also the most active analog when tested in human leukemia (K652) cells. A dose response comparison in K562 cells showed that it was more active than the unsubstituted compound over the concentration range tested ($10^{-5}$ to $10^{-2}$M). Prolactin stimulated growth of rat Nb2 lymphoma cells was inhibited by each of the compounds with p-hydroxy-3-phenylacetylamino-2,6-piperidinedione manifesting the greatest activity. Compound p-hydroxy-3-phenylacetylamino-2,6-piperidinedione was more active in Nb2 lymphoma cells than 3-phenylacetylamino-2,6 piperidinedione over the range tested ($10^{-4}$M to $10^{-3}$M).

Further analysis of growth inhibition of the most active analog p-hydroxy-3-phenylacetylamino-2,6-piperidinedione compared with the parent compound p-hydroxy-3-phenylacetylamino-2,6-piperidinedione was performed in MCF-7 (E-3) human breast cancer cells. Both 3-phenylacetylamino-2,6 piperidinedione and p-hydroxy-3-phenylacetylamino-2,6-piperidinedione inhibited estrogen simulated cell growth. In a 9 day model, p-hydroxy-3-phenylacetylamino-2,6-piperidinedione was more active than 3-phenylacetylamino-2,6 piperidinedione with $IC_{50}$ comparable to tamoxifen (3-phenylacetylamino-2,6 piperidinedione, $3 \times 10^{-5}$M; p-hydroxy-3-phenylacetylamino-2,6-piperidinedione, $7 \times 10^{-6}$M, tamoxifen, $1 \times 10^{-7}$M). The open chain hydrolysis product of 3-phenylacetylamino-2,6 piperidinedione, PAG, did not inhibit cell growth even at high concentrations (i.e., $10^{-2}$M).

Computer modeling coupled with energy calculations confirm that 3-phenylacetylamino-2,6-piperidinedione is capable of inserting between base pairs in partially unwound double stranded DNA and forming an energetically favorable complex. A hydroxyl group placed in the para position of the phenyl ring of 3-phenylacetylamino-2,6-piperidinedione enabled formation of a second hydrogen bond thereby linking both DNA strands. This added hydrogen bond resulted in a greater fit in the DNA as assessed by energy calculations, i.e., 3-phenylacetylamino-2,6-piperidinedione (61%) versus the p-hydroxy derivative p-hydroxy-3-phenylacetylamino-2,6-piperidinedione (100%). Various substitutions at the para position as well as ortho and meta positions with fluorine and chlorine did not result in a significant increase in fit compared to 3-phenylacetylamino-2,6-piperidinedione.

When the analogs of 3-phenylacetylamino-2,6-piperidinedione were synthesized and examined for the capacity to inhibit cancer cell growth, the p-hydroxy derivative, p-hydroxy-3-phenylacetylamino-2,6-piperidinedione, which was predicted to be the most active compound based upon fit into DNA was consistently found to be the most potent compound. That the capacity of the hydroxy group of p-hydroxy-3-phenylacetylamino-2,6-piperidinedione to form a second hydrogen bond to DNA was responsible for the predicted increase in activity is further supported by the lack of increased potency of p-fluoro derivative as well as other halogenated derivatives which were incapable of forming analogous hydrogen bonds. These observations demonstrate that among the compounds examined, a correlation exists between degree of fit into DNA and predicted biological potency. These findings also support the contention that stereochemical complementarity of small molecules with nucleic acids can be a powerful tool for designing new drugs.

The mode of action of these piperidinediones is still not proven. One mode of action might involve insertion into DNA as suggested by the computer modeling results and the observation that DNA synthesis measured by thymidine incorporation was significantly inhibited upon treatment with 3-phenylacetylamino-2,6-piperidinedione in Nb2 lymphoma cells. No covalent adducts of 3-phenylacetylamino-2,6-piperidinedione with DNA were detected and the binding was observed to be weak and reversible, in comparison to classical intercalating drugs. Another possible mode of action is suggested by the observation that compound p-hydroxy-3-phenylacetylamino-2,6-piperidinedione inhibits estrogen stimulated cell growth in MCF-7 cells, which is comparable to that of the established anti-estrogen tamoxifen. In contrast to tamoxifen, however, neither 3-phenylacetylamino-2,6-piperidinedione nor p-hydroxy-3-phenylacetylamino-2,6-piperidinedione exhibited appreciable binding for the estrogen receptor. At the same time, direct binding of such anti-estrogens to DNA appears to be weak. Taken as a whole, these findings support the possibility of a weak interaction of the piperidinediones with both DNA and the estrogen receptor, involving a receptor mediated insertion of the ligand into DNA.

Development of Pharmacophores

Molecular modeling, as described above, facilitates the establishment of the best fit of molecules into nucleic acids such as double-stranded DNA based on steric and electrostatic considerations. Individual molecules, such as estradiol, fit optimally into specific sites on DNA based on the location of specific nucleotides and the bonding characteristics of individual heteroatoms (see Example 2). Molecules that are related to a specific molecule such as estradiol but display chemical differences will fit into the estradiol site with different degrees of precision: some may fit better and give rise to estradiol agonistic responses while those with poor fit display weak estrogenic activity. These different molecules may be aligned relative to the docking of heteroatoms with heteroatoms on the DNA to optimize electrostatic interactions. In the creation of pharmacophores described below, molecules with activity equal to or greater than that of the hormone are chosen for alignment. To date, such molecules fit equally well or better than the hormone into DNA using the energy calculation methodology described above. Molecules which do not fit as well into DNA as the parent hormone are excluded from inclusion in the construction of the pharmacophore. The alignment of the combined surfaces of the molecules occupies a specific volume of space thereby forming a three dimensional shape.

Pharmacophores are three dimensional arrangements of chemical groups related to a given biological activity which enables meaningful comparison of molecules exhibiting the same biological function (Naruto et al., *Eur. J. Med. Chem.* 20:529–532 (1985)). Pharmacophores can be derived by simple overlap of active structures or common functional groups in the molecules. Without a way to orient the molecules e.g., based upon fit with another macromolecule—a receptor, enzyme, or in this case DNA, it is difficult and, in some cases, impossible to construct a reliable pharmacophore. This problem results in part from the fact that even closely related active molecules frequently fit into macromolecules in very different ways.

A pharmacophore, as used herein, is defined as a 3-dimensional shape having a specific volume derived from the combined van der Waals surface of active molecules oriented by fit into DNA, coupled with point charges located adjacent to the surface. A pharmacophore represents an aggregate array of positions in space of a series of molecules having the same or similar biological activity. The van der Waals surface can be represented in various ways including as a volume map, a dot surface, or a Connolly surface. The point charges are represented as dummy atoms whose positions are determined by the average positions of functional groups on active molecules which can form hydrogen bonds. Suitable charges are placed on the dummy atoms consistent with the capacity of the active molecules to form hydrogen bonds. The pharmacophores are specific for different compounds, their related molecules and a particular biological activity. According to the present invention, within the general class of molecules called hormones, an estrogen pharmacophore, an anti-estrogen pharmacophore, an androgen pharmacophore, a thyroid hormone pharmacophore, and a toxicity pharmacophore (shown in FIGS. 2–5) have been disclosed. It should be emphasized that these created pharmacophores do not exist as such in nature and are the product of aligning several related molecules to common binding sites in DNA using methods as described herein.

Many other pharmacophores have been constructed using the method described in this application. A pharmacophore, once created, stands alone and is subsequently independent from the nucleic acid that was involved in its formation. Thus, after formation of the pharmacophore, one no longer needs to use the DNA as a template for the design of biologically active molecules. The pharmacophore itself can be used to generate new molecules that will possess the same or similar structural and charge features that are represented by the pharmacophore. This is a completely different concept from the one of using the DNA as the model for the design of compounds. The pharmacophore can be used itself for any number of applications, including but not limited to the followings as a screening tool for drug development; to determine if a particular compound will possess bioactivity of a certain type, for instance estrogenic or androgenic activity; for toxicological evaluation; and to design compounds that possess increased or decreased binding affinity for DNA.

Each pharmacophore has a characteristic shape, topology, volume, and electrostatic profile. A pharmacophore is accurately described by its three dimensional shape which is represented by a coordinate system that is configured in computer memory (see FIGS. 2–5 for examples of pharmacophores. Each specific atom within a molecule that fits in a pharmacophore has a specific location relative to the docking heteroatoms. The individual atoms also have electrical charges assigned to them. These charges are represented numerically and through many other ways including the use of colors and shading to indicate field strength. As the degree of steric and electrostatic fit between the pharmacophore and the dummy atoms increases, resulting in a negative energy of interaction (-kcal), the efficacy of the pharmacophore increases which could manifest as increased bioactivity. The term "energy of interaction" as used herein is the total energy in -kcal of a molecule as it is being fitted into a pharmacophore. This has been observed in the case of molecules that fit within the estrogen pharmacophore and display bioactivity in a uterotropic assay. The volume of a pharmacophore is described in cubic angstroms. The pharmacophore can be cross sectioned precisely in any plane and internal distances measured with an angstrom ruler. The circumference of any cross section is easily measured with morphometric analysis. Similarly, specific subregions of the pharmacophore, such as the site that binds to the DNA, can be subjected to the same methods of analysis.

Construction and Utility of Pharmacophores

Figure 3:
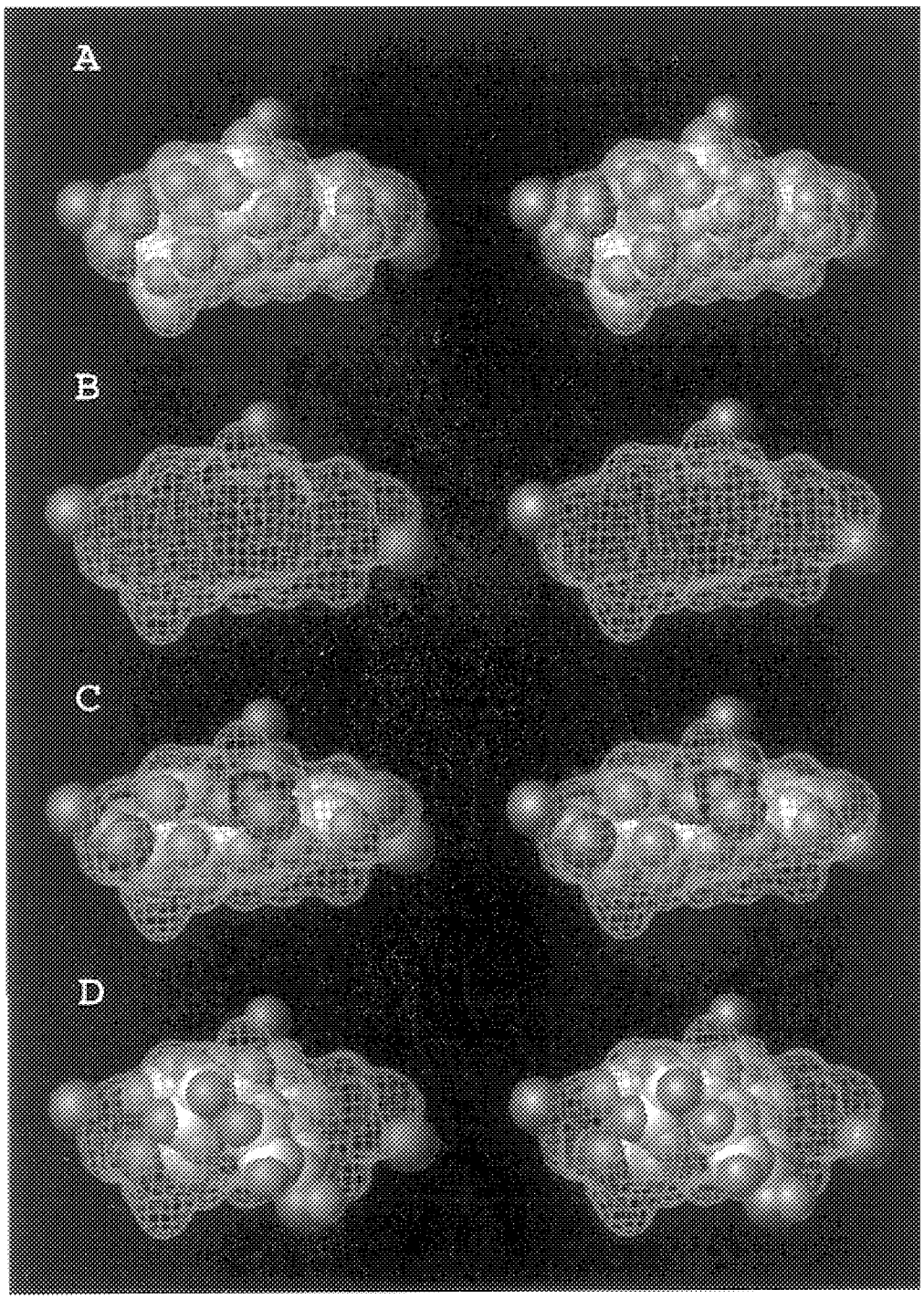
FIGS. 3A–3D depict a volume contour map (yellow) in stereo with dummy atoms (magenta) surrounding the active molecules which were used in the construction of the pharmacophore (A); the empty pharmacophore (B); fit of the highly active estrogen 3,11β,17β-trihydroxy-7α-methylestra-1,3,5(10)-triene 11-nitrate ester (hereinafter 7α-methylestradiol-11β-nitrate ester reported in Peters et al., *J. Med. Chem.* 32:2306–2310 (1989)) which is accommodated completely within the pharmacophore (C); and poor fit of the inactive estrogen 9β-estradiol which extends appreciably beyond the surface of the pharmacophore (D).
Figure 4:
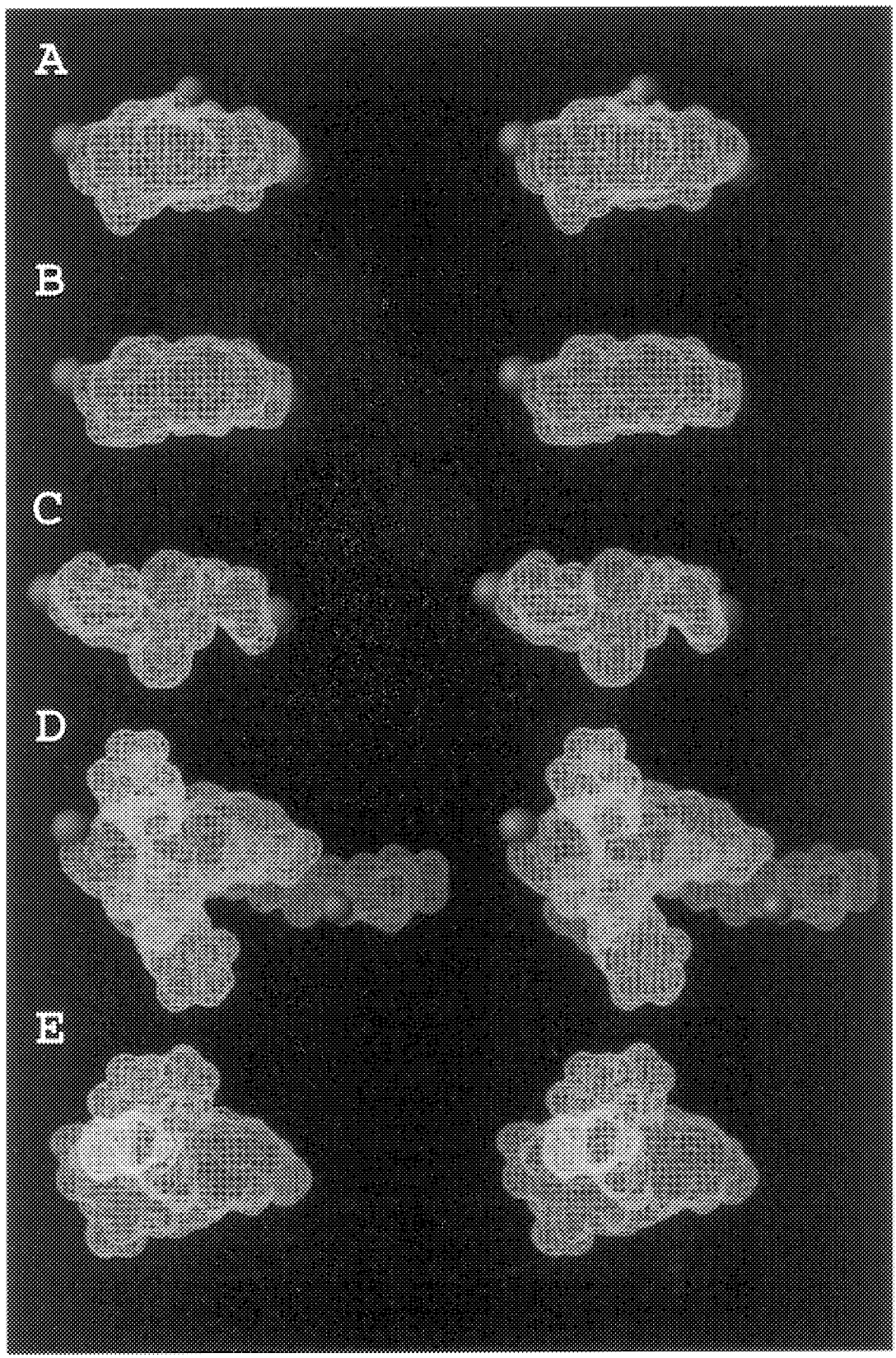
FIGS. 4A–4E depict a stereo view of volume maps (green mesh) and dummy atoms (magenta) for pharmacophores for estrogen (A), androgen (B), thyroid (C), anti-estrogen (D), and toxicity (E). Dummy atoms are not presented with the toxicity pharmacophore volume map.
Figure 5:
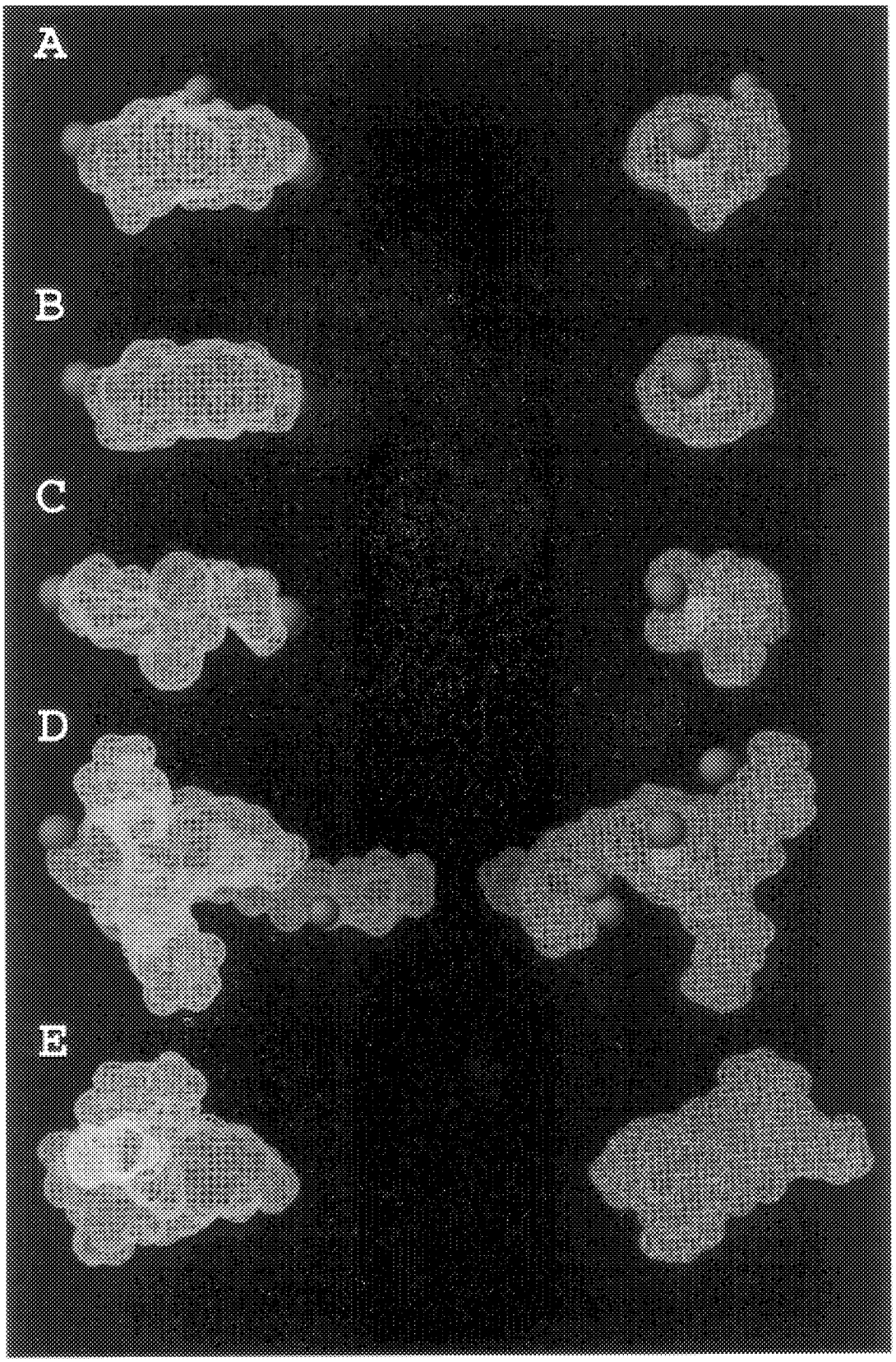
FIGS. 5A–5E, left column, shows the volume maps (green mesh) and dummy atoms (magenta) for pharmacophores for estrogen (A), androgen (B), thyroid (C), anti-estrogen (D), and toxicity (E). The right column presents an orthogonal view (90 degree rotation) of the corresponding images in the left column.

An example of the construction and utilization of the estrogen pharmacophore is given below. FIG. 2A is a computer generated space filling stereo view of the DNA cavity which fits estrogens. The fit of active estrogens oriented by energy calculations into the DNA cavity, using the methods described above, is presented in FIG. 2B. FIG. 2C shows the combined active surface of estrogens removed from the cavity in DNA that is used to construct the pharmacophore. The atoms are colored in the following manner: carbon/white; hydrogen/cyan; nitrogen/blue; oxygen/red; phosphorus/yellow. FIG. 3 demonstrates a volume contour map (yellow) in stereo with dummy atoms (magenta) surrounding the active molecules which were used in the construction of the pharmacophore (A); the empty pharmacophore (B); fit of the highly active estrogen 3,11β, 17β-Trihydroxy-7α-methylestra-1,3,5(10)-triene 11-nitrate ester (hereinafter 7α-methylestradiol-11β-nitrate ester reported in Peters et al., *J. Med. Chem.* 32:2306–2310 (1989)) which is accommodated completely within the pharmacophore (C); poor fit of the inactive estrogen 9β-estradiol which extends appreciably beyond the surface of the pharmacophore (D). FIGS. 4 and 5 present examples of the three dimensional appearance of estrogen, androgen, thyroid, antiestrogen, and toxicity pharmacophores.

Figure 6:
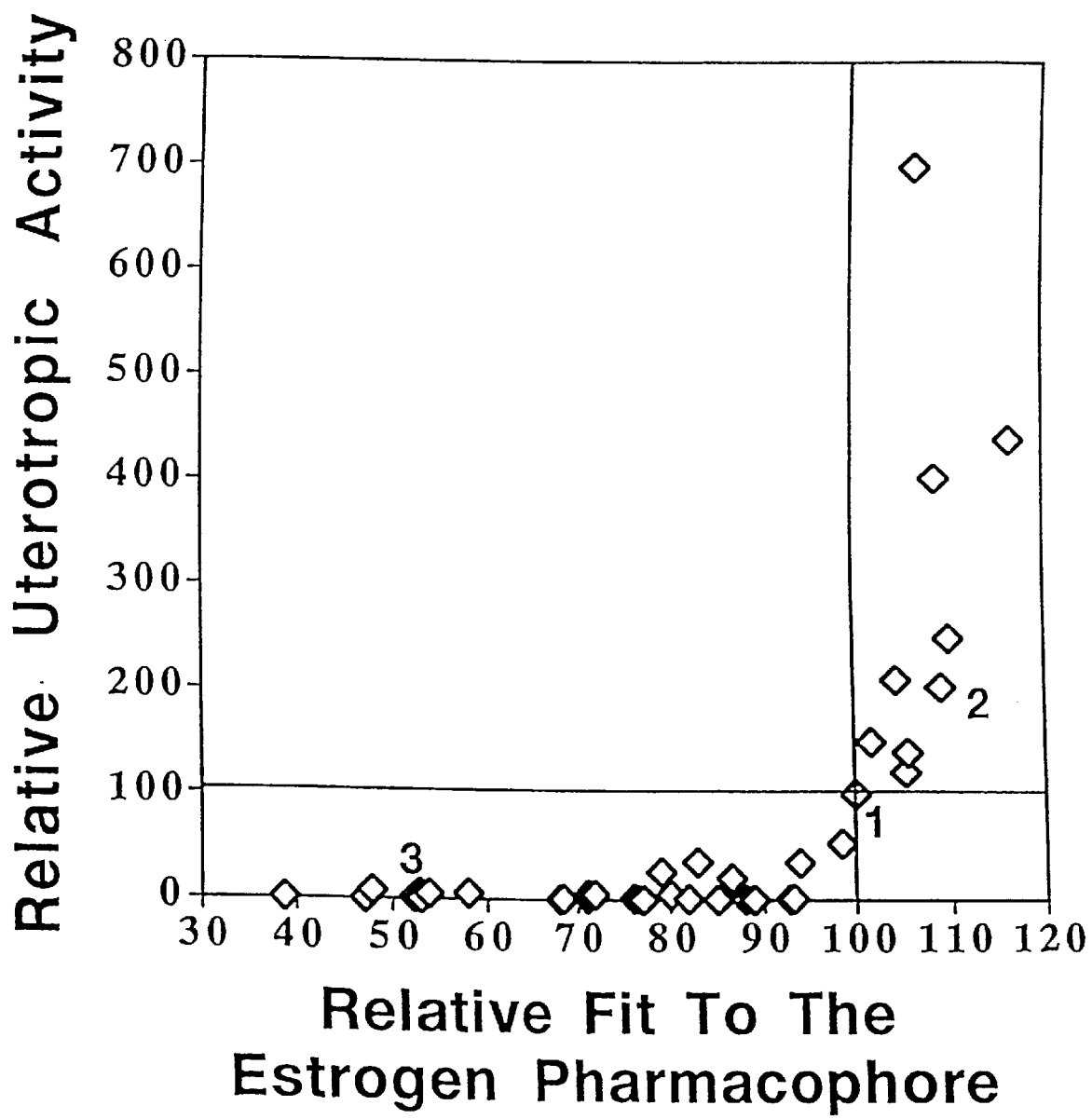
FIG. 6 demonstrates the relationship between the degree of fit of various compounds to the estrogen pharmacophore and the relative uterotropic (estrogenic) activity.

Quantitative measurements of the degree of fit of various compounds to the pharmacophore are shown in FIG. 6. Fit is determined by measuring the amount of volume of each structure which could be placed within the pharmacophore volume map and normalizing the value to that of the natural hormone estradiol set at 50%. Electrostatic interactions with the dummy atoms are optimized for each compound and calculated using the Tripos force field. The electrostatic energy value is normalized to that of estradiol set at 50%. In this study, the total of volume fit and electrostatic fit are treated equally and totaled to reflect the overall fit in the pharmacophore. As shown in FIG. 6, degree of fit to the pharmacophore correlates highly to relative uterotropic (estrogenic) activity. In comparison to estradiol, 7α-methylestradiol-11β-nitrate ester (labeled 2), which is not part of the data set used to construct the pharmacophore, fits appreciably better than estradiol (labeled 1). In contrast, 7α-methylestradiol-11β-nitrate ester binds poorly to the estrogen receptor (less than 6% of the binding of estradiol). The uterotropic values for 7α-methylestradiol-11β-nitrate ester (labeled 2) relative to estradiol set to a normalized value of 100% are considerably greater than that of estradiol (Peters et al., *J. Med. Chem.* 32:2306–2310 (1989)) as predicted by fit into the pharmacophore. In contrast, it is not possible to fit 9β-estradiol (labeled 3) into the pharmacophore and, as predicted, this analog has little uterotropic activity. In summary, fit of compounds to the pharmacophore correlates with biological activity and can thus be used to design new compounds by virtue of their fit. It is noteworthy that the highly potent estrogenic nitrate ester binds very poorly to the estrogen receptor. Thus, it would not be possible to predict the estrogenic activity of this analog on the basis of receptor binding or from a pharmacophore derived from a putative binding site in a protein receptor. In many cases, compounds with greater estrogenic activity than the natural hormone estradiol bind relatively poorly to the estrogen receptor.

The fit of compounds into DNA is consistent with, but not the same as, fit into the pharmacophores. The distinction between the DNA cavities and the pharmacophores is that the surfaces were derived from different structures, i.e. the DNA cavities from the DNA structure and the pharmacophores from the combined surfaces of active compounds. As shown in the examples and in FIGS. 2–5, the degree of fit to the pharmacophores is obtained by fit to the three dimensional map which represents the active compounds. The pharmacophores enable quantitative determination of the degree of fit to the combined surfaces of the active compounds and this information cannot be obtained from fit into DNA. Moreover, the fit of active compounds to the pharmacophore can be quantitated based upon the portion of the molecule which does not fit within the pharmacophore volume. This enables automatic assessment of predicted inactive structures.

Toxicity Pharmacophores (Toxicophores)

Pharmacophores can be constructed to represent a three dimensional shape that is predictive of toxic biological activity. Such pharmacophores, called toxicophores, have regions that would potentially damage DNA. A typical toxicophore has been constructed using, tetrodotoxin, dioxin, RU486, dilantin, thalidomide and oroflex, among other compounds. An example of this toxicophore is provided in FIGS. 4E and 5E. For example, by overlaying this toxicophore on another pharmacophore such as the estrogen phartnacophore (FIGS. 4A and 5A), a drug designer would know to avoid designing an estrogenic compound with certain molecular groups that might impart toxic activity if these groups extended into the three dimensional space occupied by the toxicophore. This approach would greatly facilitate and economize drug design by guiding the designer to avoid synthesizing estrogenic compounds that might have damaging effects on DNA as opposed to proceeding with synthesis and purification and subsequently discovering that the compound possesses dangerous toxicity.

Solvent Pharmacophores (Aquaphores)

Pharmacophores in their relationship to nucleic acids are usually surrounded by a solvent. The predominant solvent in living organisms is water and accordingly, most pharmacophores exist in an aqueous environment. Water is the preferred embodiment of the solvent pharmacophore and is termed an aquaphore. Pharmacophores, and their molecules may also be placed in non-aqueous environments for various purposes such as crystallographic studies or other analytical procedures.

In living organisms, the aqueous environment surrounding the pharmacophore also has an intimate association with the adjacent nucleic acid. This aqueous shell assists in the optimal fit of the pharmacophore into the cavity of the double stranded DNA, and has its own three dimensional shape. The optimal steric and electrostatic placement of water molecules in the space between the pharmacophore and the DNA is achieved in the present invention. This three dimensional shape is called a solvent pharmacophore, and can be described in all the ways listed above for the pharmacophores based on other molecules such as estrogen. Solvent pharmacophores assist the designer of compounds by placing limits on the dimensions of a compound designed using a particular pharmacophore as a template. In addition, solvent pharmacophores assist the creator of pharmacophores because the solvent shell or cage represented by the pharmacophore provides enhanced ability to properly align molecules relative to DNA during the creation of the pharmacophore.

Receptophore

Many molecules, such as steroid hormones, are shuttled to the nucleus by other molecules known as receptors (Tsai and O'Malley, *Ann. Rev. Biochem.* 63:451–486 (1994)). These receptors bind the hormones (called ligands), bind to the nucleic acids, for example in their DNA binding domain, and present ligands to nucleic acids such as DNA. Evidence suggests that the binding of the receptor to the DNA causes a conformational change in the DNA to facilitate insertion of the ligand (Nardulli et al., *Molec. Endocr.* 7:331–340 (1993) ). The pharmacophore concept is based on the three dimensional shape of the optimal fit of related molecules into nucleic acids such as partially unwound, double-stranded DNA. The DNA binding domain of the receptor can be modeled into a three dimensional shape based on the same principles described above for the pharmacophore. The resultant shape is termed a receptophore and is the three dimensional representation of the sites of interaction of the receptor and the nucleotides of the DNA. The DNA binding region of each receptor likely gives rise to a different receptophore. This receptophore provides a valuable tool to molecular designers interested in developing new receptors, or in modulating receptor binding to DNA.

Receptophore-Pharmacophore Pairs

The nucleic acid binding region of receptors and their ligands can be modeled as receptophores and pharmacophores, respectively. The configuration of the receptophore and its associated pharmacophore in their proper alignment relative to their respective DNA binding regions constitutes a specific pair of shapes that represents the minimal molecular unit for DNA binding and ligand insertion. Designers of compounds utilize this information to synthesize and screen molecules to modify the facility of docking and ligand insertion. Such modifications may provide a host of new therapies such as treatments for hormone dependent carcinomas of the prostate or breast.

Metabophores

Most naturally occurring compounds are derived from antecedents or precursors in a synthetic pathway and also are destined for inactivation in a catabolic pathway. Many precursors and metabolites of compounds are less active due to the addition of an extra group such as a methyl group or acetylation of a specific site. In some cases, precursors and metabolites of a molecule have different groups added sequentially to the same site on the active molecule, creating a side chain. Knowledge of a site of preferred addition or deletion of chemical groups assists in the design of molecule with enhanced or reduced activity.

These sites can be modeled relative to the pharmacophore to produce a three dimensional representation of a preferred site for modification of the molecule. This three dimensional representation, termed a metabophore, provides constraints for rational design of active and inactive variants of the parent molecules that fit into the pharmacophore. Analysis of which chemicals can effectively be added at the attachment point of the metabophore to the pharmacophore reveals the most favorable molecules to pursue for synthesis, purification and testing.

It will be appreciated that other embodiments and uses will be apparent to those skilled in the art and that the invention is not limited to these specific illustrative examples.

EXAMPLE 1

Fit Into Partially Unwound Double Stranded DNA Using the Mammalian Female Hormone Estradiol Computer modeling has demonstrated that the mammalian steroid progesterone is a remarkable "lock and key" fit into DNA at 5'-dTdG-3', 5'-dCdA-3' (FIG. 1). Each of the known x-ray crystal structures of progesterone is capable of forming two stereospecific hydrogen bonds and a stable complex measured by force-field calculations. Remarkable complementarity is evident in the complex by the overlap of hydrophilic and hydrophobic regions of the steroid and DNA. The enantiomer of progesterone which does not occur in nature does not fit. The plant hormone gibberellic acid has also been shown to fit between base pairs but in a different sequence, i.e., 5'-TdA-3', 5'-dTdA-3'. Four stereospecific hydrogen bonds are formed within the couples: ent-gibberellic acid does not fit.

The mammalian female hormone estradiol also fits in DNA (FIG. 1). Two stereospecific hydrogen bonds of approximately 2.65 Å are formed between each hydroxyl group of the steroid and phosphate oxygens on adjacent strands. The overall fit within the complex is about −59 kcal. Most alterations of the positions of the hydroxyl groups on the estratriene nucleus result in a substantial loss of potential electrostatic interactions with the DNA. Moreover, most alterations of the absolute stereochemistry of the cyclopentanophenanthrene ring pattern also result in a substantial loss of potential electrostatic interactions with the DNA. Moreover, most alterations of the absolute stereochemistry of the cyclopentanophenanthrene ring pattern also result in a poor fitting molecule. This is evident in attempting to fit 9β-estradiol into DNA. The puckering in the steroid caused by inversion of the estradiol stereochemistry at C-9 from α to β prevents complete insertion between the base pairs. Even if forced into DNA without regard to strain caused by the overlap of van der Waals surfaces, 9β-estradiol can form only a single hydrogen bond. The relative fit into DNA resulting from partial insertion of 9β-estradiol is about −17 kcal 9β-estradiol is inactive when tested in vivo for estrogenic (uterotropic) activity.

The finding that estradiol is a "lock and key" fit into DNA, although most structural alternatives to estradiol fit poorly provides further support for the premise that DNA stereochemistry contains the master blueprint for natural product structures.

EXAMPLE 2

Correlation of Estrogenic Activity with the Fit of Estrogens and Related Analogs into DNA That fit into DNA measured by energy calculations can be correlated with biologic activity was demonstrated using a series of estrogens and related synthetic analogs. The molecules which are inactive in uterotropic assays fit poorly into DNA. Molecules that fit into DNA better than estradiol are all more active than estradiol in the uterotropic assays, for example, 11β-acetoxyestradiol (approximately −68 kcal). This correlation is also observed with nonsteroidal, synthetic estrogens, such as the potent synthetic estrogen, transdiethylstilbestrol (approximately −62 kcal), which fits well, whereas the poorly active geometrical isomer cisdiethylstilbestrol (approximately −20 kcal) is a poor fit.

EXAMPLE 3

Biosynthetic Pathways Reflect Increasing Fit into DNA Whereas Inactivation Pathways Lead to Decreasing Fit into DNA Molecular modeling studies conducted with the mammalian hormone progesterone and the plant hormone gibberellic acid have shown that each step in the respective biosynthetic pathway reflects a structural change that results in increased fit in DNA. For example, when considering possible stereoisomers which could result in any given step in progesterone biosynthesis, the best fitting structure is one which was produced in nature. In sharp contrast, each step in the inactivation of progesterone eventually leading to the excreted glucuronides and sulfates resulted in the worst possible fitting stereoisomers.

The two possible dihdro reduced metabolites of the male hormone testosterone were examined for fit and correlation with biological activity. Relative to testosterone (100%), 5β-dihydrotestosterone is a poor fit (84%), whereas its epimer 5α-dihydrotestosterone fits even better than testosterone (102%). These data are consistent with published findings by Hilgar and Hummel, "The androgenic and myogenic evaluation of steroids and other compounds -assay 1", in A G Hilgard. D. J. Hummel (ed.) *Endocrine Bioassay Data, Part III*)U.S. Dept. HEW NIH 1964), that 5α-dihydrotestosterone is a highly active androgen, whereas 5β-dihydrotestosterone is essentially inactive.

In the case of the tetrahydro reduced stereoisomers of progesterone, 3α-hydroxy-5β-pregnan-20-one was a poor fit whereas its stereoisomer 3α-hydroxy-5α-pregnan-20-one was an excellent fit. The former molecule is a highly active neurosteroid, as reported by Purdy, et al., *J. Med. Chem.* 33:1572–1581 (1990). Comparison of the specific pattern of donor/acceptor linkages of 3α-hydroxy-5α-pregnan-20-one with those in the steroid/thyroid hormone superfamily demonstrated that the linkage pattern of 3α-hydroxy-5α-pregnan-20-one is unique. Compounds having such unique linkages are predicted to have unique biologic function and may be ligands for newly discovered "orphan receptors."

EXAMPLE 4

Correlation of Toxicity and "Side Effects" with Fit into DNA

Ligands that fit into more than one site in DNA have been observed to have multiple biologic actions. Both desirable and undesirable "side effects" should thus be predictable from the specific DNA sequence which a given compound fits into as well as the manner and relative degree of fit. Examples of molecules that have been observed to fit into more than one site in DNA include the psychotropics cocaine, morphine, LSD and tetrahydrocannabinoids, and certain intercalating antibiotics. For example, the monoamine oxidase inhibitor selegiline fits into the site in DNA which accommodates glucose and various oral antidiabetic drugs as reported by Rowland et al., *J. Clin. Pharmacol.* 34:80–85(1994). This observation is consistent with the finding that selegiline causes hypoglycemia in some patients. Another case is the anti-androgen anandron which fits into the site in DNA which accommodates testosterone. Because anandron fits into DNA in two orientations, i.e., in a manner similar to both androgens and anti-androgens, mixed activity is predicted for this compound. Experimental results indicate that anandron has both agonist and antagonist activities as reported by Steinsapir, et al., *The Endocrine Society* (74th Annual Meeting) 1992:109 (abs. 228).

It has also been noted that ligands which cause stress, chemical modifications and/or covalent linkages to the DNA when fit into a given site frequently possess toxicity. Examples include certain carcinogens and teratogens, e.g., thalidomide, dioxin, arene oxides, aflatoxins and some diethylstilbestrol metabolites. Another example is the anti-progestin RU486 which stresses base pair hydrogen bonds when inserted fully into the progesterone site in DNA. Similar strain is produced by other anti-progestins having the same side chains (e.g., 11β-phenylamines) raising the possibility that such features may correlate with abortifacient activity attributed to RU486 and related analogs. Observations with thalidomide enantiomers indicate that teratogenicity associated with this compound may correlate with a stereospecific effect on base pairing. An example of such a toxicity pharmacophore, called a toxicophore, is presented in FIGS. 4E and 5E and the corresponding data file is submitted on magnetic tape.

EXAMPLE 5

Design and Development of New Drugs

Using the principles described above and in the examples, new drugs can be designed or existing drugs can be redesigned while at the same time limiting potential undesirable side effects. One example of how an active drug can be designed using the technology follows:

3-Phenylacetylamino-2,6-piperidinedione (A10) is a modified amino-acid derivative, which was originally isolated from freeze-dried human urine. Despite having low toxicity, high concentrations of A10 were required to demonstrate significant growth inhibitory activity on tumor cells. The focus of the following study was to develop more potent analogs. Modeling studies demonstrated that A10 was capable of inserting into partially unwound double stranded DNA and forming a single hydrogen bond between the imino proton of the piperidinedione ring and a phosphate oxygen on a single strand. It was observed that placing a hydroxyl group at the para position of the phenyl group of A10 would enable a second hydrogen bond to form thereby substantially enhancing fit as reported by Hendry et al., *J. Steroid Biochem. Molec. Biol.* 48:495–505 (1994), the teachings of which are hereby incorporated by reference in their entirety. The relative fit of A10 (normalized to 100%) and various related analogs measured by energy calculations demonstrate that the best fitting compound is p-OH-A10 (164%). Subsequent synthesis of these compounds followed by testing in various animal and human tumor cells demonstrated that p-OH-A10 was the most active compound and was as much as an order of magnitude more active than A10, as reported by Hendry, et al., *Recent Advances in Chemotherapy*, Buchner and Rubinstein (eds) 2498–2499 (1991), Hendry et al., U.S. Pat. No. 5,238,947 which is incorporated herein by reference.

EXAMPLE 6

Comparison of the Drug Design Technology to Clasical Structure-Activity Methods

The drug design technology described here can be used in conjunction with quantitative-structure-activity-relationship methods (QSAR), e.g., comparative field molecular analysis (CoMFA). One value of the approach is that it facilitats the orientation of various ligands relative to one another in three dimensions. The successful structure-activity relationship found for estrogens derived from fit into DNA is described here. If one were to attempt to derive such a relationship a priori without first knowing the detailed three-dimensional structure of an appropriate macromolecule (e.g., the ligand binding site of a receptor or an enzymatic site), chemical intuition would necessitate searching for common features that exist in known active structures. In the case of the natural hormone estradiol and the potent synthetic estrogen trans-diethylstilbestrol, such a common feature is the phenoxy group. Alterations of the phenoxy group give rise to inactive structures. If one overlaps the resulting three dimensional orientation with that which is obtained by optimal docking of these molecules into DNA, a different pattern emerges. Thus, one would expect that such different orientations when used subsequently to correlate activity of other molecules would give very different results. In fact, analysis of relative fit into DNA in kcal shows that if the orientation of trans-diethylstilbestrol based upon overlapping the A ring of estradiol is used to dock the ligand into DNA, a relatively poor fit results. In this case, poor activity for trans-diethylstilbestrol would be incorrectly predicted. In contrast, using the orientation of DES derived only from the stereochemistry of DNA as taught by the present invention, increased activity would be correctly predicted.

EXAMPLE 7

Design of an Anti-Estrogen, Para-Hydroxyphenylacetylamino-2,6-Piperidinedione, a Regulator of Yumor Cell Growth Within the past few years there has been a growing interest in nontoxic, naturally occurring small molecules as regulators of tumor cell growth. Examples of recently published findings include: regression of mammary carcinomas by a dietary monocyclic nonoterpens, limonene; modulation of oncogene expression in erythroleukemic cells growth by an endogenous product of lipid peroxidation, 4-hydroxynonenal; inhibition of malignant cell growth by the endogenous ligand p-hydroxyphenylacetate; and induction of tumor cell differentiation in premalignant and malignant cells by a circulating component of human plasma, phenylacetate.

Phenylacetate has been shown to reduce levels of the myc oncogene which is involved in the development of several cancers including breast, brain, prostate, blood, lung and colon. Another mechanism by which phenylacetate is thought to be effective is by reducing levels of the amino acid glutamine. Phenylacetate conjugates with circulating glutamine to produce the excreted urinary metabolite phenylacetylglutamine (PAG). Cancer cells require glutamine for growth and are known to be more sensitive to glutamine depletion that normal cells. These findings have led to the initiation of Phase I clinical trials with phenylacetate in brain and prostate cancer at the National Cancer Institute.

In the process of screening fractions of freeze dried human urine for growth inhibitory activity in human breast cancer cells, a dehydration product of PAG was isolated. The compound was characterized as 3-phenylacetylamino-2,6-piperidinedione by spectroscopic methods and independent synthesis and was termed A10 based upon the chromatographic fraction from which it was isolated. It has not been conclusively determined whether this structure is a circulating compound, however, it is similir to phenylacetate in that it lacks toxicity in both laboratory animals and humans. The compound has also been found to inhibit growth in a variety of cancer cells in vitro, as well as human breast cancer transplanted into athymic nude mice. Chemoprevention effects have also been reported. In addition to phenylacetate and methyl p-hydroxyphenylacetate, there is a number of synthetic compounds with antitumor activities that have structural features in common with 3-phenylacetylamino-2, 6-piperidinedione. Examples of such compounds in which analogies to the piperidinedione ring are prominent include the aromatase inhibitors aminoglutethimide, rogletimide and related analogs which are used in the treatment of breast cancer; the alkylating drug PCNU which inhibits tumor growth by proposed interaction with DNA; 5-cinnamoyl-6-aminouracil derivatives which inhibit tumor growth via putative DNA intercalation; amonafide and its congeners which mediate topoisomerase II DNA cleavage by intercalation, bis (2,6-dioxopiperazine) derivatives, e.g., ICRF-193, which are potent, direct inhibitors of mammalian DNA topoisomerase II.

Relative high doses of 3-phenylacetylamino-2,6-piperidinedione have been generally required to inhibit tumor growth both in vitro and in vivo. The goal of this study was to identify more active phenylacetylamino-2,6-piperidinediones using the technique described above. The technology is based upon modeling of the stereospecific fit of molecules into DNA and has been recently modified to take advantage of computer graphics and energy calculations. Computer modeling was followed by the design, synthesis, and in vitro biological testing of 3-phenylacetylamino-2,6-piperidinedione derivatives. The molecule predicated to be the most active based upon degree of fit in DNA, i.e., the p-hydroxy derivative, was found to be the most active antitumor agent in all of the biological assays investigated. When tested in MCF-7 (E3) human breast cancer cells, the p-hydroxy derivative possessed antiestrogenic activity in the range of the drug tamoxifen which is currently in clinical use for the treatment of breast cancer.

EXAMPLE 8

Figure 7A:
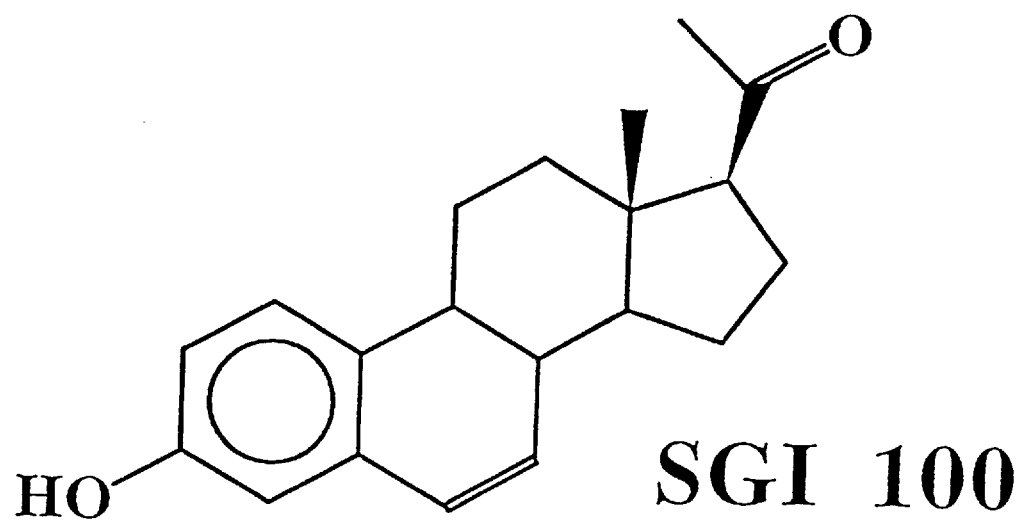
FIGS. 7a–7c show the chemical structures of three separate molecules, SGI 100, SGI 101, and SGI 102 designed with pharmacophore technology.
Figure 7B:
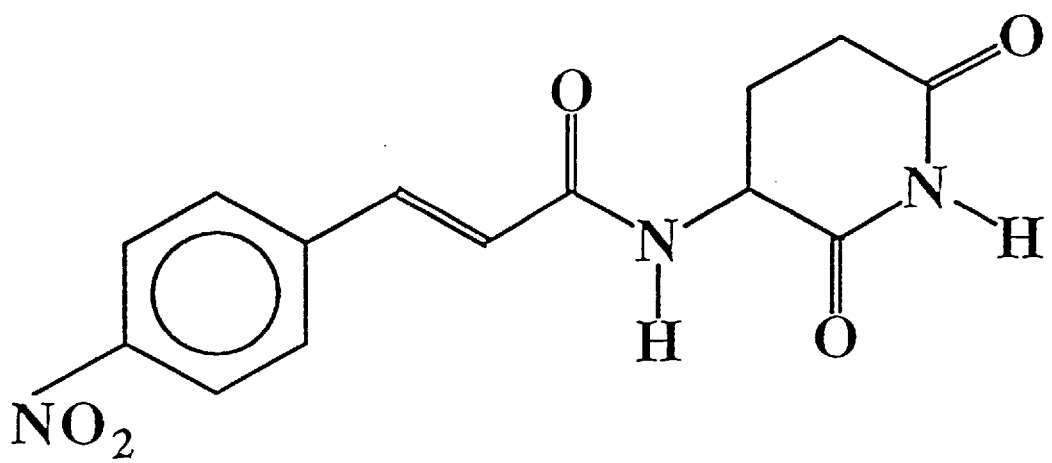
Figure 7C:
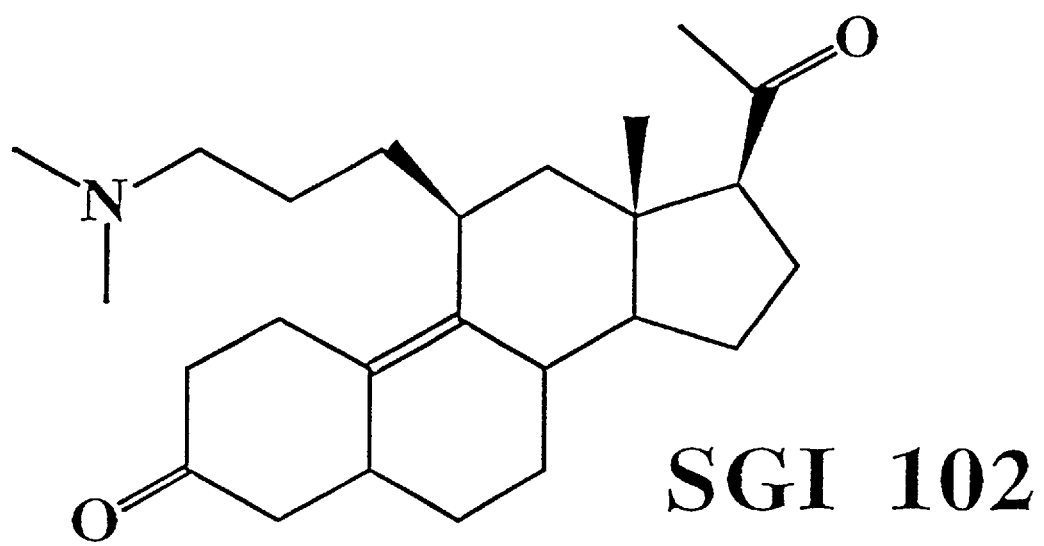

Three separate molecules designed with modeling technology are shown in FIG. 7. These molecules, termed SGI 100, SGI 101 and SGI 102 bear similarities and differences to each other. They all show structural similarities to components of both estrogen and progesterone. SGI 100 was designed on the basis of its ability to fit into the site in DNA which accommodates both estradiol and progesterone. The manner in which it fits predicted antagonist activity. When fit to the estrogen pharmacophore (FIG. 2), the acetyl group at the 17β position extended out of the pharmacophore and had electrostatic repulsion with dummy atoms (−131 kcal) compared to estrogen (−51 kcal). Accordingly, this high positive energy of interaction indicates that SGI 100 acts as an antagonist. The binding of SGI 100 to the estrogen receptor is dose dependent and approximately 144 times less than estradiol. In bioactivity experiments, SGI 100 significantly decreased cell growth in MCF-7 human breast cancer cells (134,431 cells) at a dose of $10^{-8}$M when compared to control cells (252,197 cells). The same concentration of tamoxifen citrate decreased the number of MCF-7 cells to 187,759. Thus, the design of this compound based on the pharmacophore approach of this invention predicted a demonstrable anti-estrogen bioactivity that was greater than tamoxifen. SGI 100 binds in a dose dependent manner to the progesterone receptor but with 133 to 200 times less affinity.

SGI 101 was designed on the basis of fitting into DNA at the site which accommodates estradiol but with opposite hydrogen bonding properties which predict estrogen antagonist activity. SGI 101 extends beyond the estrogen pharmacophore and has electrostatic repulsion between the para-nitro group and dummy atoms. SGI 101 is the most potent analog designed by the technology as measured by growth inhibition of MCF-7 cells. At a dose of $10^{-8}$M, SGI 101 inhibited cell growth (81,103 cells) relative to control (252, 197 cells) and was substantially more active than the same concentration of tamoxifen (187,759 cells).

SGI 102 was designed on the basis of its fit into DNA at the site which accommodates progesterone. SGI 102 possesses an alkyl amino side chain at the 11β position which extends out of the site between base pairs into the major groove. It has different hydrogen bonding properties than progesterone and would extend beyond the volume map of the progesterone pharmacophore. As such, it is predicted to be an antagonist. SGI 102 was designed prospectively, synthesized, and tested in various biological assays. SGI 102 binds in a dose dependent manner to the progesterone receptor but not as strongly as progesterone or the abortifacient antiprogestin RU486. In animal experiments, SGI 102 showed no abortifacient activity. However, in experiments using MCF-7 human breast cancer cells, SGI 102 had equivalent activity to RU486 in inhibiting growth. These findings are consistent with the predictions made by the modeling technology.

It should be understood that the foregoing relates only to a preferred embodiment of the present invention and that numerous modifications or alterations may be made therein without departing from the spirit and the scope of the invention as set forth in the appended claims.

I claim:

1. A computer-based method for comparing energies of interaction of two molecules with a nucleic acid, the method be useful in designing a molecule with a desired biological activity, comprising the computer implemented steps of:

choosing a first molecule with the desired biological activity;

determining a site comprising a nucleic acid sequence which accommodates the first molecule;

calculating an energy of interaction between the first molecule and the site;

designing a second molecule which fits into the site; and calculating an energy of interaction between the second molecule and the site to determine if the second molecule has an equal or lower energy of interaction than the first molecule for the site, wherein the second molecule has the desired biological activity if the energy of interaction of the second molecule for the site is equal to or lower than the energy of interaction of the first molecule for the site.

2. The computer-based method of claim 1 wherein the nucleic acid is selected from the group consisting of deoxyribonucleic acid, double stranded deoxyribonucleic acid, ent-deoxyribonucleic acid, ribonucleic acid, double stranded ribonucleic acid, complexes of deoxyribonucleic acid and ribonucleic acid, complexes of ribonucleic acid and ribonucleic acid, and apurinic and apyrimidinic sites.

3. The computer-based method of claim 1 wherein the nucleic acid is deoxyribonucleic acid.

4. The computer-based method of claim 2 wherein the nucleic acid is double stranded deoxyribonucleic acid and the sequence is 5'-dTdG-3', 5'-dCdA-3'.

5. The computer-based method of claim 2 wherein the nucleic acid is double stranded deoxyribonucleic acid and the sequence is 5'-dTdA-3', 5'-dTdA-3'.

6. The computer-based method of claim 2 wherein the double stranded deoxyribonucleic acid is partially unwound.

7. The computer-based method of claim 1 wherein the biological activity is hormonal, neurotransmitter, metabolic, genetic, immunologic, pathologic, toxic, anti-diabetic, or anti-mitotic.

8. The computer-based method of claim 7 wherein the biological activity is hormonal and the hormonal activity is estrogenic, anti-estrogenic, androgenic, anti-androgenic, progestational, anti-progestational, mineralocorticoid, retinoid, vitamin D-like, thyroid, ecdysone-like, gibberellic acid-like, or glucocorticoid hormonal activity.

9. The computer-based method of claim 1 wherein the first molecule has a cyclopentanophenanthrene motif.

10. The computer-based method of claim 1 wherein the second molecule has a cyclopentanophenanthrene motif.

11. The computer-based method of claim 1 wherein the site in the nucleic acid which accommodates the first molecule and the second molecule is determined by the computer-implemented method further comprising:

using a stereoviewer for docking the first molecule and the second molecule in the site; and using van der Waals dot, mesh, and space filling surfaces to guide the docking of the molecules and to minimize steric strain of the nucleic acid.

12. The computer-based method of claim 1 wherein the calculation of the energy of interaction between the first molecule and the site comprises the computer-implemented steps of:

calculating a value for steric fit by optimizing van der Waals interactions of the first molecule with the nucleic acid;

calculating a value for hydrogen bonding fit by measuring a change in electrostatic energy using charges on donor hydrogens and acceptor heteroatoms; and adding the calculated values.

13. The computer-based method of claim 1 wherein the calculation of the energy of interaction between the second molecule and the site comprises the computer-implemented steps of:

calculating a value for steric fit by optimizing van der Waals interactions of the second molecule with the nucleic acid;

calculating a value for hydrogen bonding fit by measuring a change in electrostatic energy using charges on donor hydrogens and acceptor heteroatoms; and adding the calculated values.

14. A computer-based method for comparing energies of interaction of two molecules with a nucleic acid the method being useful in predicting a biological activity of a molecule, comprising the computer implemented steps of:

choosing a first molecule with the biological activity;

determining a site comprising a nucleic acid sequence which accommodates the first molecule;

calculating an energy of interaction between the first molecule and the site;

determining whether a second molecule fits into the site; and calculating an energy of interaction between the second molecule and the site to determine if the second molecule has an equal or lower energy of interaction than the first molecule for the site, wherein the second molecule has the desired biological activity it the energy of interaction of the second molecule for the site is equal to or lower than the energy of interaction of the first molecule for the site.

15. The computer-based method of claim 14 wherein the nucleic acid is selected from the group consisting of deoxyribonucleic acid, double stranded deoxyribonucleic acid, ent-deoxyribonucleic acid, ribonucleic acid, double stranded ribonucleic acid, complexes of deoxyribonucleic acid and ribonucleic acid, complexes of ribonucleic acid and ribonucleic acid, and apurinic and apyrimidinic sites.

16. The computer-based method of claim 15 wherein the nucleic acid is deoxyribonucleic acid.

17. The computer-based method of claim 15 wherein the nucleic acid is double stranded deoxyribonucleic acid and the sequence is 5'-dTdG-3', 5'-dCdA-3'.

18. The computer-based method of claim 15 wherein the nucleic acid is double stranded deoxyribonucleic acid and the sequence is 5'-dTdA-3', 5'-dTdA-3'.

19. The computer-based method of claim 15 wherein the double stranded deoxyribonucleic acid is partially unwound.

20. The computer-based method of claim 14 wherein the biological activity is hormonal, neurotransmitter, metabolic, genetic, immunologic, pathologic, toxic, anti-diabetic, or anti-mitotic.

21. The computer-based method of claim 20 wherein the biological activity is hormonal and the hormonal activity is estrogenic, anti-estrogenic, androgenic, anti-androgenic, progestational, anti-progestational, mineralocorticoid, retinoid, vitamin D-like, thyroid, ecdysone-like, gibberellic acid-like, or glucocorticoid hormonal activity.

22. The computer-based method of claim 14 wherein the first molecule has a cyclopentanophenanthrene motif.

23. The computer-based method of claim 14 wherein the second molecule has a cyclopentanophenanthrene motif.

24. The computer-based method of claim 14 wherein the site in the nucleic acid which accommodates the first molecule and the second molecule is determined by docking the first molecule and the second molecule in the site comprising use of van der Waals dot, mesh, and space filling surfaces to guide the docking of the first molecule and the second molecule and to minimize steric strain of the nucleic acid.

25. The computer-based method of claim 14 wherein the site in the nucleic acid which accommodates the first molecule and the second molecule is determined by a method further comprising the computer-implemented steps of:

using a stereoviewer for docking the molecules in the site; and using van der Waals dot, mesh, and space filling surfaces to guide the docking of the molecules and to minimize steric strain of the nucleic acid.

26. The computer-based method of claim 14 wherein the calculation of the energy of interaction between the first molecule and the site comprises the computer-implemented steps of:

calculating a value for steric fit by optimizing van der Waals interactions of the molecule with the, nucleic acid;

calculating a value for hydrogen bonding fit by measuring a change in electrostatic energy using charges on donor hydrogens and acceptor heteroatoms; and adding the calculated values.

27. The computer-based method of claim 14 wherein the calculation of the energy of interaction between the second molecule and the site comprises the computer-implemented steps of:

calculating a value for steric fit by optimizing van der Waals interactions of the molecule with the nucleic acid;

calculating a value for hydrogen bonding fit by measuring a change in electrostatic energy using charges on donor hydrogens and acceptor heteroatoms; and adding the calculated values.

28. The method of claim 1, further comprising the step of synthesizing the second molecule.

29. A molecule made with the method of claim 28 having the structure of:

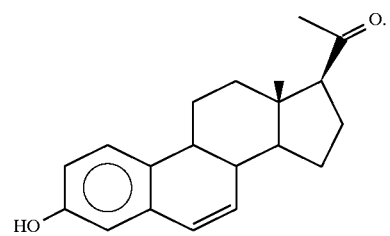

30. A molecule made with the method of claim 28 having the structure of:

31. A molecule made with the method of claim 28 having the structure of:
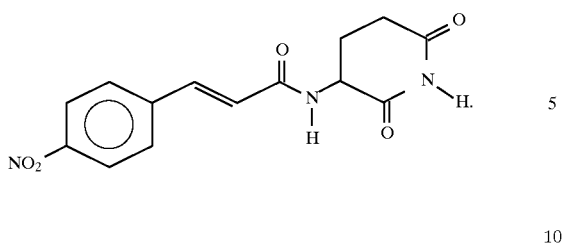
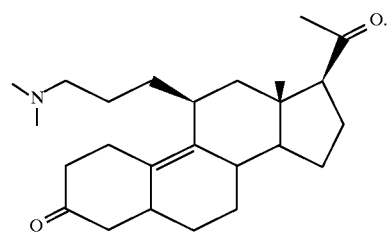

UNITED STATES PATENT AND TRADEMARK OFFICE
CERTIFICATE OF CORRECTION

PATENT NO. : 5,888,741
DATED : March 30, 1999
INVENTOR(S) : Lawrence B. Hendry

It is certified that error appears in the above-identified patent and that said Letters Patent is hereby corrected as shown below:

At column 8, line 35, after the word receptor, please insert --.--.
At column 8, line 37, after the word DNA, please insert --.--.

At column 19, line 65, please delete "Yumor", and insert therefor --Tumor--.
In Claim 1, at column 22, line 4, please delete "be", and insert therefor --being--.
In Claim 14, at column 23, line 36, after the word activity, please delete "it", and insert therefor --if--.
In Claim 26, at column 24, line 31, after the words with the, please delete ",".

Signed and Sealed this

Fourteenth Day of March, 2000

Attest:

Q. TODD DICKINSON

Attesting Officer

Commissioner of Patents and Trademarks